(12) United States Patent
Shah

(10) Patent No.: US 9,295,447 B2
(45) Date of Patent: Mar. 29, 2016

(54) SYSTEMS AND METHODS FOR IDENTIFYING VASCULAR BORDERS

(75) Inventor: Jignesh Shah, Folsom, CA (US)

(73) Assignee: Volcano Corporation, San Diego, CA (US)

( * ) Notice: Subject to any disclaimer, the term of this patent is extended or adjusted under 35 U.S.C. 154(b) by 1260 days.

(21) Appl. No.: 13/212,004

(22) Filed: Aug. 17, 2011

(65) Prior Publication Data

US 2013/0046167 A1    Feb. 21, 2013

(51) Int. Cl.
| | | |
|---|---|---|
| A61B 8/08 | (2006.01) | |
| A61B 8/12 | (2006.01) | |
| A61B 5/00 | (2006.01) | |
| A61B 5/02 | (2006.01) | |

(52) U.S. Cl.
CPC ............. *A61B 8/0883* (2013.01); *A61B 5/0035* (2013.01); *A61B 5/0095* (2013.01); *A61B 8/0891* (2013.01); *A61B 8/12* (2013.01); *A61B 8/5215* (2013.01); *A61B 5/02007* (2013.01)

(58) Field of Classification Search
CPC ...... A61B 8/0883; A61B 8/0891; A61B 8/12; A61B 8/5215
See application file for complete search history.

(56) References Cited

U.S. PATENT DOCUMENTS

| | | | |
|---|---|---|---|
| 4,917,097 A | 4/1990 | Proudian et al. | |
| 5,368,037 A | 11/1994 | Eberle et al. | |
| 5,453,575 A | 9/1995 | O'Donnell et al. | |
| 5,603,327 A | 2/1997 | Eberle et al. | |
| 5,779,644 A | 7/1998 | Eberle et al. | |
| 5,857,974 A | 1/1999 | Eberle et al. | |
| 5,876,344 A | 3/1999 | Baker et al. | |
| 5,921,931 A | 7/1999 | O'Donnell et al. | |
| 5,938,615 A | 8/1999 | Eberle et al. | |
| 6,033,357 A | 3/2000 | Ciezki et al. | |
| 6,049,958 A | 4/2000 | Eberle et al. | |
| 6,080,109 A | 6/2000 | Baker et al. | |
| 6,123,673 A | 9/2000 | Eberle et al. | |
| 6,165,128 A | 12/2000 | Cespedes et al. | |
| 6,283,920 B1 | 9/2001 | Eberle et al. | |
| 6,309,339 B1 | 10/2001 | Ciezki et al. | |
| 6,457,365 B1 | 10/2002 | Stephens et al. | |
| 6,712,767 B2 | 3/2004 | Hossack et al. | |
| 6,725,081 B2 | 4/2004 | Ciezki et al. | |
| 6,767,327 B1 | 7/2004 | Corl et al. | |
| 6,776,763 B2 | 8/2004 | Nix et al. | |
| 6,779,257 B2 | 8/2004 | Kiepen et al. | |
| 6,780,157 B2 | 8/2004 | Stephens et al. | |
| 6,899,682 B2 | 5/2005 | Eberle et al. | |
| 6,962,567 B2 | 11/2005 | Eberle et al. | |

(Continued)

FOREIGN PATENT DOCUMENTS

| | | |
|---|---|---|
| WO | WO 2008/100386 A2 | 8/2008 |
| WO | WO 2011/053931 A2 | 5/2011 |

OTHER PUBLICATIONS

B Wang et al. Intravascular Photoacoustic Imaging. IEEE J Quantum Electron. Jun. 3, 2010; 16(3): 588-599.*

(Continued)

*Primary Examiner* — Amanda Lauritzen Moher
(74) *Attorney, Agent, or Firm* — Haynes and Boone, LLP

(57) ABSTRACT

A method comprises gathering intravascular photoacoustic (IVPA) data using a transducer inserted into a vessel of a patient. The method further includes modulating the IVPA data to determine a first tissue border and displaying a border map representing the first tissue border.

21 Claims, 2 Drawing Sheets

(56) References Cited

U.S. PATENT DOCUMENTS

| | | | |
|---|---|---|---|
| 6,976,965 | B2 | 12/2005 | Corl et al. |
| 7,097,620 | B2 | 8/2006 | Corl et al. |
| 7,215,802 | B2 | 5/2007 | Klingensmith et al. |
| 7,226,417 | B1 | 6/2007 | Eberle et al. |
| 7,359,554 | B2 | 4/2008 | Klingensmith et al. |
| 7,463,759 | B2 | 12/2008 | Klingensmith et al. |
| 7,641,480 | B1 | 1/2010 | Hossack et al. |
| 7,676,910 | B2 | 3/2010 | Kiepen et al. |
| 7,711,413 | B2 | 5/2010 | Feldman et al. |
| 7,736,317 | B2 | 6/2010 | Stephens et al. |
| 2005/0196026 | A1* | 9/2005 | Klingensmith .... A61B 5/02007 382/128 |
| 2007/0036404 | A1 | 2/2007 | Li |
| 2008/0146918 | A1* | 6/2008 | Magnin et al. ............. 600/437 |
| 2008/0177183 | A1* | 7/2008 | Courtney ............ A61B 5/0062 600/463 |
| 2008/0287795 | A1 | 11/2008 | Klingensmith et al. |
| 2010/0028261 | A1* | 2/2010 | Emelianov et al. ............ 424/9.1 |
| 2011/0021924 | A1* | 1/2011 | Sethuraman et al. ......... 600/463 |
| 2012/0271170 | A1* | 10/2012 | Emelianov et al. ............ 600/439 |

OTHER PUBLICATIONS

S Emelianov et al. Intravascular Ultrasound and Photoacoustic Imaging. IEEE (c)2008.*

A Iskurt et al. Identification of Luminal and Medial Adventitial Borders in Intravascular Ultrasound Images Using Level Sets. Springer-Verlag Berlin Heidelberg (c)2006.*

International Search Report and Written Opinion received in corresponding Patent Cooperation Treaty Application No. PCT/US2012/050565, dated Jan. 31, 2013, 9 pages.

Li-Shen, Jimmy, et al. Photoacoustic imaging of coronary artery stents, Department of Biomedical Engineering, The University of Texas at Austin, Austin, TX 78712, USA, vol. 17, No. 22, Optics Express, published Feb. 28, 2008, published Oct. 19, 2009, pp. 19894-19901.

Sethuraman, S., et al., Development of a combined intravascular ultrasound and photoacoustic imaging system, Department of Biomedical Engineering, The University of Texas at Austin, Austin, TX 78712, USA, Photons Plus Ultrasound: Imaging and Sensing 2006: The 7$^{th}$ Conference on Biomedical Thermoacoustics, Optoacoustics, and Acousto-optics, Proc. of SPIE vol. 6086, 60860F (2006), pp. 60860F-1-60860F-9.

Sethuraman, S., et al., Intravascular photoacoustic imaging of atherosclerotic plaques: ex vivo study using a rabbit model of atherosclerosis, Department of Biomedical Engineering, The University of Texas at Austin, Austin, TX 78712, USA, Photons Plus Ultrasound: Imaging and Sensing 2007: The Eighth Conference on Biomedical Thermoacoustics, Optoacoustics, and Acousto-optics, Proc. of SPIE vol. 6437, 643729 (2007), pp. 643729-1-643729-9.

Sethuraman, Shriram., et al., Spectroscopic intravascular photoacoustic imaging to differentiate atherosclerotic plaques, Department of Biomedical Engineering, The University of Texas at Austin, Austin, TX 78712, USA, vol. 16, No. 5, Optics Express, published Feb. 28, 2008, pp. 3362-3367.

Wang, Bo, et al., Spectroscopic intravascular photoacoustic imaging to differentiate atherosclerotic plaques, Department of Biomedical Engineering, The University of Texas at Austin, Austin, TX 78712, USA, vol. 18, No. 5, Optics Express, published Feb. 24, 2010, pp. 4889-4897.

* cited by examiner

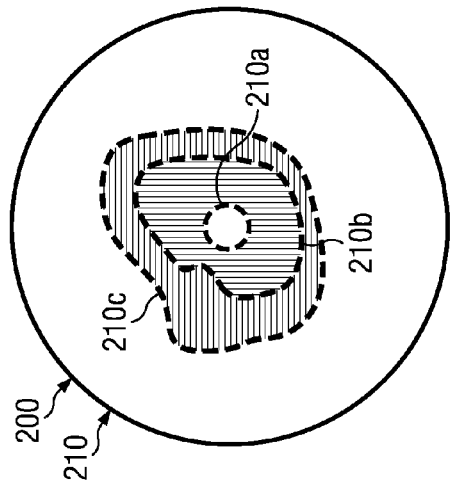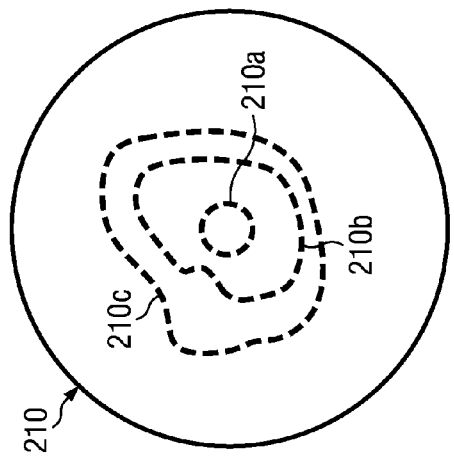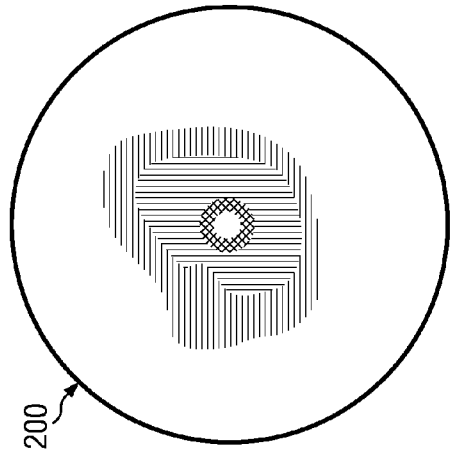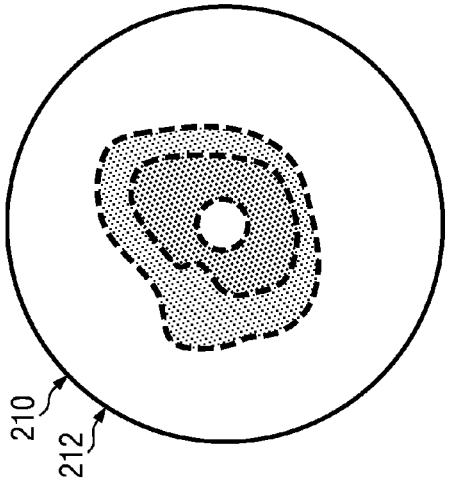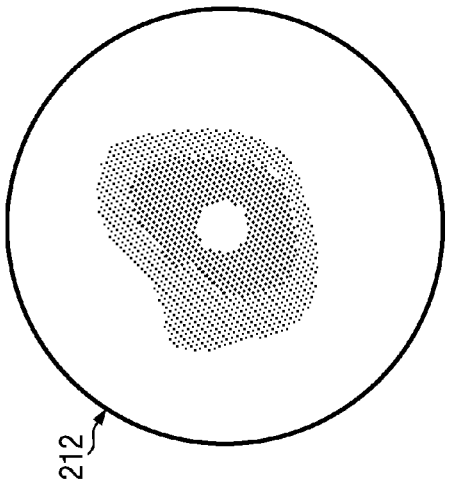

SYSTEMS AND METHODS FOR IDENTIFYING VASCULAR BORDERS

TECHNICAL FIELD

Embodiments of the present disclosure relate generally to the field of medical devices and, more particularly, to the use of intravascular imaging systems to identify a vascular border.

BACKGROUND

In the United States and many other countries, heart disease is a leading cause of death and disability. One particular kind of heart disease is atherosclerosis, which involves the degeneration of the walls and lumen of the arteries throughout the body. Scientific studies have demonstrated the thickening of an arterial wall and eventual encroachment of the tissue into the lumen as fatty material builds upon the vessel walls. The fatty material is known as "plaque." As the plaque builds up and the lumen narrows, blood flow is restricted. If the artery narrows too much, or if a blood clot forms at an injured plaque site (lesion), flow is severely reduced, or cut off and consequently the muscle that it supports may be injured or die due to a lack of oxygen. Atherosclerosis can occur throughout the human body, but it is most life threatening when it involves the coronary arteries which supply oxygen to the heart. If blood flow to the heart is significantly reduced or cut off, a myocardial infarction or "heart attack" often occurs. If not treated in sufficient time, a heart attack often leads to death. Further, the weakening of vessel walls can lead to an aneurysm or swelling of the vessel that, if left untreated, will rupture and lead to internal bleeding and often death. Aneurysms commonly occur in the aorta.

The medical profession relies upon a wide variety of tools to treat heart conditions and major vessel diseases, ranging from drugs to minimally invasive procedures to open heart "bypass" surgery. Often, a lesion can be diagnosed and treated with minimal intervention through the use of catheter-based tools that are threaded into the coronary arteries via the femoral artery in the groin. For example, one treatment for lesions is a procedure known as percutaneous transluminal coronary angioplasty (PTCA) whereby a catheter with an expandable balloon at its tip is threaded into the lesion and inflated. The underlying lesion is re-shaped, and hopefully, the lumen diameter is increased to improve blood flow. In the case of aortic aneurysms, an endovascular aortic repair (EVAR) or thoracic endovascular aortic repair (TEVAR) may be utilized to introduce a stent graft into the vasculature. Such techniques have traditionally relied on CT scans performed before surgery and angiograms during surgery to identify important anatomical features of the vasculature associated with the interventions. However, the information from a CT scan is often inaccurate at the time of surgery since the aneurysm or other condition is continually evolving over time.

In recent years, a technique has been developed for obtaining detailed information about coronary and peripheral vessels. The technique, known as Intravascular Ultrasound (IVUS), employs one or more very small transducers arranged towards the end of a catheter to provide electronically transduced echo signals to an external imaging system in order to produce a two or three-dimensional image of the lumen, the vessel tissue, and/or the tissue surrounding the vessel. These high quality images are generated in substantially real time. The IVUS images allow a user to view the form and structure of a site within a vessel rather then merely determining that blood is flowing through a vessel.

Another technique recently developed for imaging vasculature is known as Intravascular Photoacoustic (IVPA) imaging. With this technique, light energy is directed at the vascular tissue which causes the tissue to oscillate and create sound waves. These sound waves may be detected by a transducer for use in producing an image of the vascular tissue.

While the existing devices and methods have been generally adequate for their intended purposes, they have not been entirely satisfactory in all respects. The imaging catheters, systems, and associated methods of the present disclosure overcome one or more of the shortcomings of the prior art.

SUMMARY

In one embodiment, a method comprises gathering intravascular photoacoustic (IVPA) data using a transducer inserted into a vessel of a patient. The method further includes modulating the IVPA data to determine a first tissue border and displaying a border map representing the first tissue border.

In another embodiment, a system comprises a catheter including an elongated flexible body having a lumen extending along its length from a proximal portion to a distal portion and a transducer positioned adjacent the distal portion. The transducer is configured to gather intravascular photoacoustic (IVPA) data. The system further includes a program executable by a computer and configured to modulate the IVPA data to determine a first tissue border of a vessel and to prepare a border map representing the first tissue border.

In another embodiment, a method comprises providing an imaging probe for use in a vessel. The imaging probe includes at least one transducer configured to gather intravascular photoacoustic (IVPA) data and intravascular ultrasound (IVUS) data. The method further comprises generating an IVPA image using the IVPA data and generating an IVUS image using the IVUS data. The method further includes coregistering the IVPA and IVUS images to display a combined image. The method includes modulating the IVPA data to identify a first border of a tissue type of the vessel and displaying a border map representing the first border on the combined image.

BRIEF DESCRIPTION OF THE DRAWINGS

FIG. 3 illustrates an intravascular photoacoustic (IVPA) image.

FIG. 4 illustrates a vascular border map image.

FIG. 5 illustrates a combined image of the IVPA and vascular border map images.

FIG. 6 illustrates an intravascular ultrasound (IVUS) image.

FIG. 7 illustrates the combined image of the IVUS and vascular border map images.

DETAILED DESCRIPTION

Figure 1:
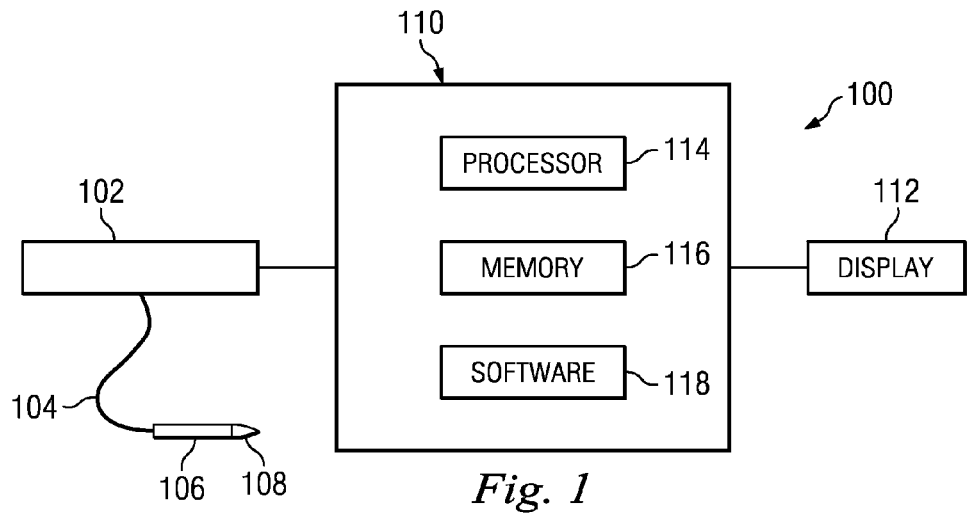
FIG. 1 is a vascular border identification system in accordance with one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

Referring first to FIG. 1, a vascular border identification system 100 according to one embodiment of the present disclosure includes a control console 102 connected via a catheter 104 to an imaging probe 106. The distal end of the imaging probe 106 includes a transducer 108. In use, the imaging probe is inserted into a blood vessel of a patient and gathers data about the vascular tissue through signals received by the transducer 108. The data is received by the control console 102 and provided to a computer 110 for storage and processing. An image representing the data is displayed on a display device 112. The display device 112 may be integrated into the control console 102 or may be a separate piece of equipment.

The control console 102 may include one or more components for controlling the function of the imaging probe 106 and receiving data from the probe. In the present embodiment, the control console 102 is an integrated console including both intravascular photoacoustic (IVPA) component and an intravascular ultrasound (IVUS) components. In alternative embodiments, the control console may include an optical coherence tomography (OCT) component, an MRI component, a thermographic component, or any other modality of an imaging component known in the art.

The computer 110 includes a processor 114 and a memory device 116. The computer 110 is operable to execute a software program 118 for analyzing data from the imaging probe 106 and for preparing information for display on the display device 112. The computer 110 may be a personal computer, programmable logic device, or any other data processing device that is known in the art. The computer 110 may further include other software or hardware, such as input/output devices and networking devices, known in the art. In the present embodiment, the imaging probe 106 is an integrated imaging probe which allows for both IVUS and IVPA imaging. For IVUS imaging, the transducer 108 provides both a signal transmission and a signal reception function. Specifically, the transducer transmits ultrasonic waves, such as radio frequency (RF) waves, and receives echo waves backscattered from the vascular tissue. The transducer 108 may include a piezoelectric transducer, a piezoelectric micro-machined ultrasonic transducer (PMUT), a polyvinylidene fluoride (PVDF) transducer, or any other transducer device known in the art.

IVUS data may be gathered in segments, either through a rotating transducer or an array of circumferentially positioned transducers, where each segment represents an angular portion of the resultant image. Thus, it takes a plurality of segments to image an entire cross-section of a vascular object. Furthermore, multiple sets of IVUS data may be gathered from multiple locations within a vascular object, for example, by moving the transducer linearly through the vessel. These multiple sets of data can then be used to create a plurality of two-dimensional (2D) or three-dimensional (3D) images. In some embodiments, one or more motors may be used to rotate or linearly move the transducer to obtain the data segments.

In some instances, the IVUS imaging equipment includes components similar or identical to those found in IVUS products from Volcano Corporation, such as the Eagle Eye® Gold Catheter, the Visions® PV8.2F Catheter, the Visions® PV 018 Catheter, and/or the Revolution® 45 MHz Catheter, and/or IVUS products available from other manufacturers. Further, in some instances the catheter system 100 includes components or features similar or identical to those disclosed in U.S. Pat. Nos. 4,917,097, 5,368,037, 5,453,575, 5,603,327, 5,779,644, 5,857,974, 5,876,344, 5,921,931, 5,938,615, 6,049,958, 6,080,109, 6,123,673, 6,165,128, 6,283,920, 6,309,339; 6,033,357, 6,457,365, 6,712,767, 6,725,081, 6,767,327, 6,776,763, 6,779,257, 6,780,157, 6,899,682, 6,962,567, 6,976,965, 7,097,620, 7,226,417, 7,641,480, 7,676,910, 7,711,413, and 7,736,317, each of which is hereby incorporated by reference herein, in its entirety.

For IVPA imaging, the imaging probe 106 includes a light transmitting device capable of transmitting photons and a signal receiving device capable of receiving acoustic signals. The transducer 108 may function to receive both the returned IVUS and IVPA acoustic signals or a separate IVPA transducer may be used. When the light transmitting device is directed at vascular tissue and photons are emitted, the tissue begins to oscillate and create sound waves. These sound waves may be detected by the transducer. The light transmitting device includes a light source, such as a laser, and a light transmission guide such as one or more optical fibers. Further, in some instances the catheter system 100 includes components or features similar or identical to those described in U.S. patent application Ser. No. 12/449,384 which is incorporated herein by reference in its entirety. Integrated IVUS/IVPA probes are disclosed in U.S. patent application Ser. No. 12/449,384 and International App. No. PCT/US2010/055006, both of which are hereby incorporated by reference herein, in their entirety.

In an alternative embodiment, certain components of the integrated IVUS/IVPA probe may be separated. For example, the light transmitting source may be supplied by a separate probe. With a separated light transmitting source, the light may be transmitted from within the vessel, from outside the vessel, or from outside the body.

In the present embodiment, the catheter 104 includes a lumen which allows the catheter to pass over a guide wire (not shown). The imaging probe 106 further includes a lumen which allows it to pass over the guide wire.

Figure 2:
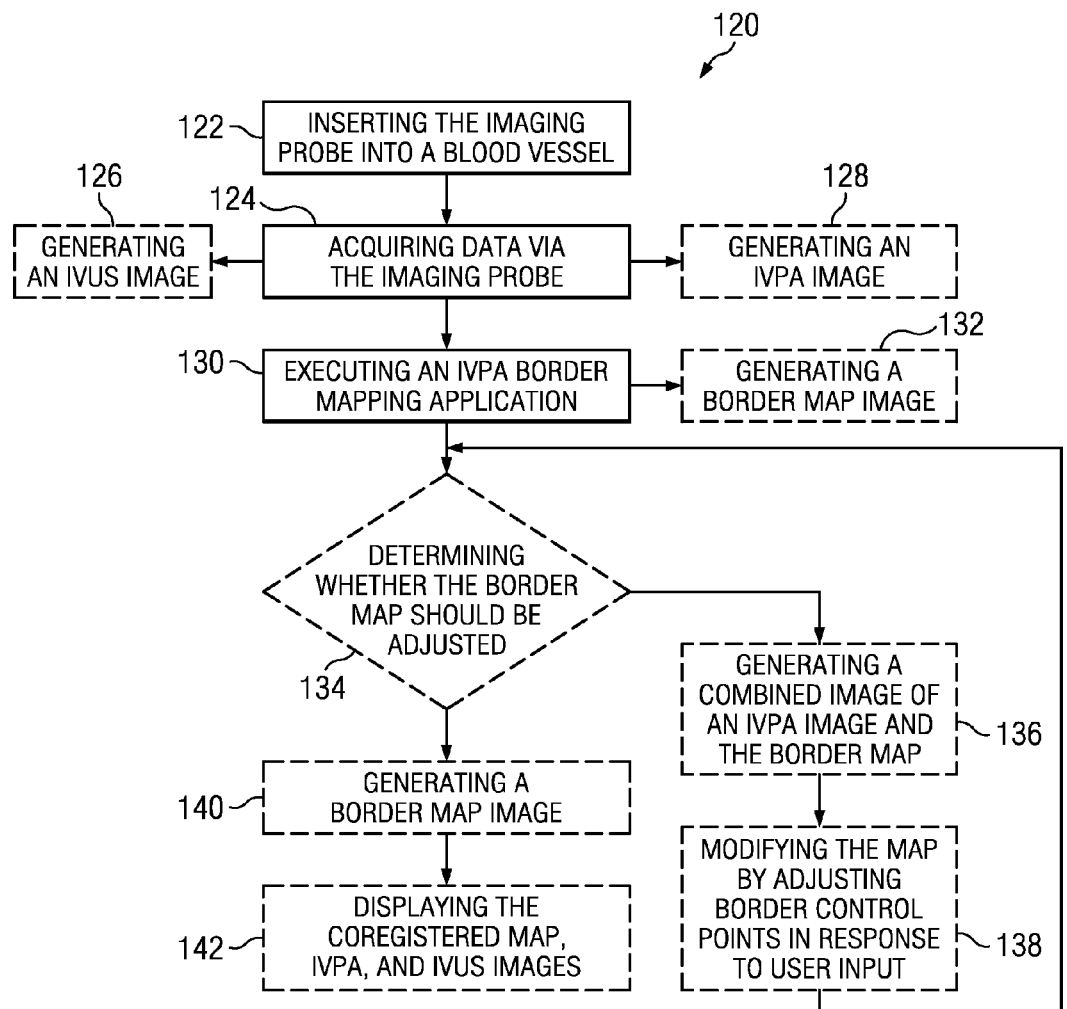
FIG. 2 illustrates a method for identifying a vascular border in accordance with one or more embodiments of the present disclosure.

In one embodiment, the vascular border identification system 100 may be utilized as shown in the method 120 of FIG. 2 to determine the borders of various vascular tissue. Use of the system according the described method may provide important clinical information to a user physician. For example, a determination of the tissue borders can be used to determine the extent of stenosis and coronary disease progression. Such a determination can be used to further determine whether additional procedures such as angioplasty or atherectomy are indicated or whether more invasive procedures are warranted.

A method 120 includes the step 122 of inserting the imaging probe 106 into a blood vessel. The imaging probe 106 and catheter 104 may be routed along a guide wire extending into the blood vessel. The blood vessel may be an artery but the term encompasses any structure of the cardiovascular system of a human or animal. In alternative embodiments, an imaging probe may be directed through other body passages including lymphatic vessels, the esophagus, stomach, intestines, ureter, urethra, trachea, sinuses, Eustachian tubes, bile ducts, or pancreatic ducts. After the imaging probe 106 is located within the blood vessel, IVPA and IVUS signals are transmitted by the imaging probe. As previously noted, in some alternative embodiments, the light transmitting source for the IVPA system may be located outside the blood vessel.

At step 124, IVPA and IVUS data is collected via the imaging probe 106 and received by the computer 110 through the control console 102. Optionally, at step 126, an IVUS image 212 (FIG. 6) of the blood vessel is displayed. Optionally, at step 128, an IVPA image 200 (FIG. 3) of the blood vessel is displayed. The IVUS and IVPA images may be displayed on the same display device by toggling between the two images. Alternatively, the images may be displayed on different display devices. In still another alternative, the images may be co-registered and displayed together, at the same time, one a single display device.

At step 130, the computer 110 executes a border mapping application to identify the location of borders between various tissue types such as intima, medial, and adventitial vascular tissue; blood tissue; and plaque tissue (including calcified tissues, fibrous tissues, calcified-necrotic tissues and fibro-lipidic tissues). For example, the border mapping application may identify the location of the luminal border which demarcates the blood-intima interface or the location of the medial-adventitial border which demarcates the boundary between the media and advnetitia tissues.

Specifically, the border mapping application modulates the IVPA data using multiple data processing operations applied serially, in parallel, or a combination thereof. In one embodiment, the data modulation utilizes one or more features of the IVPA image 200 of the blood vessel to generate a border map 210 depicting a catheter border 210a, a luminal border 210b, and a medial-adventitial border 210c (FIG. 4). The border map 210 may include a plurality of border control points 210d. The border map, including the border points, may be displayed using a graphic image uniquely distinguishable from an IVPA or IVUS image. For example, solid or dashed lines, graphic markers, and colored map regions may be used to graphically represent the border map on an IVPA or IVUS image. The use of graphics, including for markers or map regions, may correspond to a key indicating the predetermined meanings of the colors or the markers.

Different tissue types will generate different photoacoustic responses. These differences can identified by changes in pixel color of IVPA images or changes in gradient in or intensity of IVPA images. These changes on the images can be used to identify border points and develop the border map. Additionally or alternatively, data modulation may include reference to predetermined and stored information about the characteristics of the tissue types. Additionally or alternatively, the data modulation utilizes a plurality of initial filtering operations having different filter coefficients and filter pass band characteristics. The output of the initial filtering operations is used to generate a secondary IVPA image. The secondary image is further filtered to generate a binary map showing the potential locations of border points along the vascular border. The border points may be used to generate the border map. The IVPA image may be filtered based upon characteristics such as signal intensity, slope, or changes in gradient/intensity. The filtering operations may be performed in parallel or in multiple stages. Data modulation may be performed by hardware or software. For example, in one embodiment, field programmable gate arrays (FGPA's) or custom application-specific integrated circuits (ASIC's) could be used to perform the data modulation in hardware. In another alternative, the data modulation may be performed using analog components or using micro-controllers or a graphics card. In yet another alternative, the data modulation may be performed in software. The data modulation may be in real time or generated after a delay.

Optionally, at step 132, the border map image 210 is displayed either alone (FIG. 4) or in co-registration with the IVPA image 200 (FIG. 5).

Optionally, at step 134, a determination is made as to whether a user modification application should be used. The determination may be made by a user or may be prompted by the computer, for example if a portion of the computer generated border map could not be determined using data modulation. At step 136, the combined image of the IVPA image 200 and the border map image 210 is displayed on a display device for viewing by a user. At step 138, user input may be used to modify the border map 210 by adjusting one or more border control points 210d of the border map. It should be noted that the number, location, and size of the control points of the border map image 210 are illustrative only and should not be limiting. The border control points may be manually repositioned in that the user may select and move one of the control points with an input device (e.g. a mouse, a touch screen, key strokes). Further details may be found in U.S. Pat. Pub. No. 2008/0287795, which is incorporated by reference in its entirety herein.

Optionally, at step 140, the modified border map image is displayed. Optionally, at step 142, the border image 210 and the IVUS image 212 are coregistered and displayed (FIG. 7). The IVPA image 200 may also be coregistered with the border image 210 and the IVUS image 212 for displaying a combined image on the display device. In embodiments in which the IVPA and IVUS data is captured by a common imaging probe using a common transducer or using separate transducers fixed in relationship (time and space) to each other, the IVPA and IVUS images can be coregistered by superimposing one image on the other. In other embodiments, where the IVPA and IVUS data are captured by different probes in a non-fixed relationship, coregistration may be performed using a marker or indicia. For example, the IVPA probe acquires one or more markers and the IVUS probe acquires the same one or more markers. Based upon the alignment of the one or more markers, the separately acquired images can be coregistered.

Coregistration and concurrent display IVUS and IVPA images may be useful because the images provide different information to the viewer. Generally, IVUS images display the mechanical properties of the tissue. For example, with IVUS, it is possible to observe structures deep within the tissue where acoustic mismatches generate reflections. IVPA displays the optical properties of the tissue. For example, different plaque types will have different optical properties, and thus generate different responses. Both IVUS and IVPA generate images from the same region using different properties, both of which can be important in clinical assessments.

Although the border mapping process has been described using IVPA and IVUS imaging modalities, it is understood that the same general steps could be applied using other modalities such as OCT or MRI.

Although illustrative embodiments have been shown and described, a wide range of modification, change, and substitution is contemplated in the foregoing disclosure and in some instances, some features of the present disclosure may be employed without a corresponding use of the other features. It is understood that such variations may be made in the foregoing without departing from the scope of the present disclosure. Accordingly, it is appropriate that the appended claims be construed broadly and in a manner consistent with the scope of the present disclosure.

What is claimed is:

1. A system comprising:
a catheter including an elongated flexible body having a lumen extending along its length from a proximal portion to a distal portion and a transducer positioned adjacent the distal portion, the transducer configured to gather intravascular photoacoustic (IVPA) data and intravascular ultrasound (IVUS) data;
a computer operable to:
receive IVPA data and IVUS data obtained by the transducer while the catheter is positioned within a vessel of a patient;
process the IVPA data to generate an IVPA imam
process the IVUS data to generate an IVUS image;
coregister the IVPA and IVUS images to prepare a combined image;
process the IVPA data to determine a first tissue border of a vessel and prepare a border map based on the IVPA data, wherein the border map is distinguishable from the IVUS image and the IVPA image, and wherein the border map comprises a loop graphically accentuating the first tissue border; and
output the combined image and the border map based on the IVPA data to a display in communication with the computer.

2. The system of claim 1 wherein the computer is operable to coregister the border map, the IVPA image, and the IVUS image to prepare the combined image.

3. The system of claim 1 wherein the transducer is one in an array of transducers.

4. The system of claim 1 wherein the transducer includes a piezoelectric element.

5. The system of claim 1 wherein the transducer includes a piezoelectric micro-machined ultrasonic transducer.

6. The system of claim 1 wherein the transducer includes a polyvinylidene fluoride transducer.

7. The system of claim 1 wherein the border map represents the luminal border.

8. The system of claim 1 wherein the border map represents the medial-adventitial border.

9. The system of claim 1 wherein the computer is operable to process the IVPA data to determine a second tissue border of a vessel and to prepare a border map representing the first and second tissue borders.

10. The system of claim 1 wherein the catheter further includes a light transmitting source.

11. The system of claim 10 wherein the light transmitting source is a laser.

12. A method comprising:
introducing an intravascular probe into a vessel of a patient, the intravascular probe including an elongated flexible body having a proximal portion and a distal portion, wherein the intravascular probe further includes a transducer positioned adjacent to the distal portion of the flexible body, wherein the transducer is configured to obtain intravascular photoacoustic (IVPA) data and intravascular ultrasound (IVUS) data;
receiving, at a computer in communication with the intravascular probe, the IVPA data and the IVUS data obtained by the transducer while the intravascular probe is positioned within the vessel of the patient;
generating, using the computer, an IVPA image using the IVPA data;
generating, using the computer, an IVUS image using the IVUS data;
coregistering, using the computer, the IVPA and IVUS images to generate a combined image;
processing, using the computer, the IVPA data to identify a first border of a tissue type of the vessel; and
providing the combined image and a border map based on the IVPA data and distinguishable from the IVPA image and the IVUS image from the computer to a display in communication with the computer, wherein the border map comprises a loop graphically accentuating the first border on the combined image.

13. The method of claim 12 wherein the border map includes border control points and the method further includes modifying the location of the border control points in response to user input.

14. The method of claim 12 wherein the step of displaying the border map includes depicting a gradient change at the location of the first border.

15. The method of claim 12 wherein the step of displaying the border map includes depicting a color change at the location of the first border.

16. The method of claim 12 further comprising processing the IVPA data to identify a second border of another tissue type of the vessel and displaying the border map representing the first and second borders on the combined image.

17. The method of claim 12, wherein the first border is the luminal border.

18. The method of claim 12 wherein the first border is the medial-adventitial border.

19. The method of claim 12 wherein the step of processing the IVPA data includes filtering the IVPA data.

20. The method of claim 12 further comprising controlling a light transmitting source to illuminate the vessel.

21. The method of claim 20 wherein the intravascular probe further comprises the light transmitting source.

* * * * *